Sept. 6, 1949. E. PRUSHEK Plant Pat. 871
CHRYSANTHEMUM PLANT
Filed Nov. 28, 1947
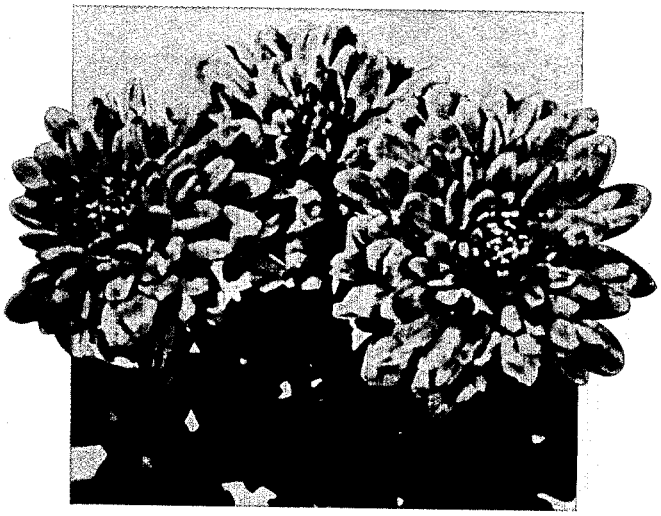
Inventor:
Emil Prushek
By Robbins & Robbins
Attorneys Patented Sept. 6, 1949 Plant Pat. 871

UNITED STATES PATENT OFFICE

871

CHRYSANTHEMUM PLANT

Emil Prushek, Niles, Mich., assignor to The R. M. Kellogg Company, Three Rivers, Mich., a corporation of Michigan Application November 28, 1947, Serial No. 788,743

1 Claim. (Cl. 47—60)

My present invention comprises a new and distinct variety of chrysanthemum plant, the result of crossing the variety "Princess" of Plant Patent No. 711, and an unnamed chrysanthemum seedling.

The objects of my invention, in general, were to produce a new variety of chrysanthemum having the dwarf, compact, and floriferous characteristics of the bush or plant form similar to those of the variety "Princess," but having blossoms whose general color effect was a near approach to pink; and to produce such a new variety having a high degree of frost resistance in the petals to withstand early frost.

I have conducted a program of careful selection and cross-breeding for the purposes of accomplishing the objects just mentioned, and as a part of a broader program of selection and cross-breeding which I have been conducting for some time with a view to producing new varieties of chrysanthemums having the dwarf and compact habits of growth above mentioned in varieties of different desired colors in reference to the blooms of such plants.

Now the result of the specific hybridization above mentioned has been to produce my present new and distinct variety of chrysanthemum characterized by its dwarf and compact habits of growth, its early flowering, its long season due to the long color life of individual blooms, its resistance to frost, and the purple color of its blooms.

More specifically, the blooms of my new variety are Magnolia Purple in color. In dimensions, the plants of my new variety have an average height of 9'' and an average diameter of 15'', in reference to first year plants from soft top cuttings under uniform culture in the region of Berrien County, Michigan.

The plants of my new variety of chrysanthemum are very dwarf and compact, resembling very closely in form and habit of growth the parent variety "Princess."

While my new variety is similar to its parent "Princess" in reference to habit of growth and the form of the plant, my new variety differs from both of its parents in reference to the color of its bloom, the parent variety "Princess" having sunset colored blooms and the unnamed seedling parent having white blooms, while the blooms of my new variety are Magnolia Purple in color.

The plants of my new variety have a high degree of frost resistance, such that the petals of the blooms withstand the early frost. In the breeding work preceding the specific cross by which my new variety was obtained as above described, the highly frost-resistant variety "Jewell" was used twice for the purpose of procuring frost resistance in my new variety. Plants of my new variety successfully withstand temperatures down to 28° F. with ice formation, and under such conditions there was no damage to open flowers.

Of the older chrysanthemum varieties, my new variety most nearly resembles "Major Cushion." However, my new variety is ten days earlier in flowering than "Major Cushion." The pompom blooms of my new variety have better substance and more orderly shape and arrangement of petals than "Major Cushion," and the color of the blooms of my new variety, being Magnolia Purple, differs from the color of the blooms of "Major Cushion," which is Lilac Purple. "Major Cushion" makes a larger plant having dimensions of 14'' average height and 20'' average diameter, as compared with the smaller dimensions in reference to my new variety of plant above mentioned. Thus my new variety has about one-fourth of the size or mass of the similar "Major Cushion."

My new variety is early flowering, has a long blooming season, and the blooms have long lasting color life, being similar in these characteristics, to the present variety "Princess" of Plant Patent 711.

My new variety has been found to retain its distinctive characteristics through successive asexual reproduction.

The accompanying drawing forming a part hereof shows a spray of typical blossoms of my new variety.

The following is a detail description of my new variety, all color references being to the Horticultural Colour Chart of the British Colour Council, observations being made on plants grown in Berrian County, Michigan.

Classification: Botanic—*Chrysanthemum hortorum.*

*Flower*

Blooming habit: Blooms early; profusely. *Recurrent*—continuous in the fall.

Bud:

*Size.*—Small.

*Form.*—Short with flat top; globular.

Not affected by wet weather.

Not affected by hot weather.

*Color.*—When sepals first divide—Magnolia Purple o30/2. When petals begin to unfurl—Magnolia Purple o30. When half blown: inside of petals—Magnolia Purple o30; reverse of petals—Magnolia Purple o30/2.

*Sepals.*—Smooth edge; stand up.

*Calyx.*—Shape—apple; size—broad; small; aspect—smooth.

*Peduncle.*—Bud opens well; not affected by adverse conditions.

Bloom:

*Size.*—Small; average size when fully expanded, 1½″.

*Borne.*—Singly.

*Stems.*—Medium; normal.

*Form.*—When first open—flat. Permanence—retains its form to the end.

*Petalage.*—Very double. Number of petals under normal conditions, about 200.

*Color.*—Center of flower—Magnolia Purple o30/1. Outer petals—Magnolia Purple o30/2. Base of petals (singlet)—Primrose Yellow 601/1. Inside of petals—Magnolia Purple o30/1. Reverse of petals—Magnolia Purple o30/3. General tonality from a distance—Magnolia Purple o30/1 and o30/2, halfway between.

*Discoloration.*—First week—no change. Second week—a pleasant fading toward white (Magnolia Purple o30/3). Third week—same as above.

Petals:

*Texture.*—Thin; soft. Slight fading from wet weather. Not affected by hot weather.

*Appearance.*—Velvety inside and outside.

*Form.*—Oval; notched.

*Arrangement.*—Imbricated.

*Fragrance.*—Characteristic chrysanthemum.

*Lastingness.*—On the plant—very long. As cut flower—very long.

Genital organs:

*Stamens, anthers.*—Small; few. Color—yellow.

*Stamens, filaments.*—Short. Color—lemon yellow.

*Pollen.*—Gold yellow.

*Styles.*—Columnar; medium; thin.

*Stigmas.*—Yellow.

*Plant*

*Form.*—Bush.

*Growth.*—Medium; dwarf; compact.

Foliage:

*Size.*—Small.

*Quantity.*—Normal.

*Color.*—Upper side—normal green; under side—light green. *Old foliage*—upper side—dark green; under side—normal green.

*Shape.*—Oval pointed; acutely lobed.

*Texture.*—Upper side—velvety; flat; under side—velvety. Ribs and veins—light.

*Edge.*—Serrated.

*Serration.*—Double.

*Leaf stem.*—Color—green. Under side—smooth.

*Stipules.*—None.

Wood:

*New wood.*—Color, reddish. *Old wood.*—Color, brown.

I claim:

A new and distinct variety of crysanthemum plant characterized as to novelty by its dwarf, compact growth, its early flowering, its long blooming season, the long color life of its blooms, its resistance to frost, and the purple color of its flowers, substantially as described and illustrated.

EMIL PRUSHEK.

No references cited.